United States Patent
Kaminski

(10) Patent No.: US 12,130,214 B2
(45) Date of Patent: Oct. 29, 2024

(54) ENVIRONMENTAL GROUNDWATER SAMPLING SYSTEM

(71) Applicant: Q.E.D. Environmental Systems, Inc., Dexter, MI (US)

(72) Inventor: David B. Kaminski, Clayton, CA (US)

(73) Assignee: Q.E.D. ENVIRONMENTAL SYSTEMS, INC., Dexter, MI (US)

( * ) Notice: Subject to any disclaimer, the term of this patent is extended or adjusted under 35 U.S.C. 154(b) by 222 days.

(21) Appl. No.: 17/793,131

(22) PCT Filed: Feb. 26, 2021

(86) PCT No.: PCT/US2021/019805
§ 371 (c)(1),
(2) Date: Jul. 15, 2022

(87) PCT Pub. No.: WO2021/173924
PCT Pub. Date: Sep. 2, 2021

(65) Prior Publication Data
US 2023/0341299 A1 Oct. 26, 2023

Related U.S. Application Data

(60) Provisional application No. 62/981,626, filed on Feb. 26, 2020.

(51) Int. Cl.
*G01N 1/14* (2006.01)
*G01N 33/18* (2006.01)

(52) U.S. Cl.
CPC ............... *G01N 1/14* (2013.01); *G01N 33/18* (2013.01)

(58) Field of Classification Search
CPC ........ G01N 1/14; G01N 33/18; G01N 2001/14
(Continued)

(56) References Cited

U.S. PATENT DOCUMENTS

| 3,504,742 A | 4/1970 | Crawford |
| 4,015,072 A | 3/1977 | Gillemot |

(Continued)

FOREIGN PATENT DOCUMENTS

| EP | 1222360 A1 | 7/2002 |
| KR | 20120023267 A | 3/2012 |

(Continued)

OTHER PUBLICATIONS

International Preliminary Report on Patentability for PCT Application Serial No. PCT/IB2020/054394, dated Nov. 18, 2021, 15 pages.

(Continued)

*Primary Examiner* — Robert R Raevis
(74) *Attorney, Agent, or Firm* — Kinney & Lange, P.A.

(57) ABSTRACT

A system for sampling groundwater from a well that includes a pump configured to be at least partially submerged in the groundwater within the well and pump the groundwater out of the well, a sensor configured to output a signal indicative of the depth of the groundwater in the well, and a controller in communication with the sensor. The controller is configured to receive the signal indicative of the depth of the groundwater from the sensor and compensate for groundwater ingress into the well by adjusting a rate of flow of groundwater pumped by the pump based on the signal to stabilize the depth of groundwater in the well while the pump is pumping groundwater from the well.

17 Claims, 3 Drawing Sheets

(58) Field of Classification Search
USPC ........ 73/64.56, 152.18, 152.28, 863, 863.02, 73/863.03, 864, 864.34, 864.35, 864.73, 73/864.81; 166/250.01, 264; 417/73
See application file for complete search history.

(56) References Cited

U.S. PATENT DOCUMENTS

| | | | |
|---|---|---|---|
| 4,026,355 | A | 5/1977 | Johnson et al. |
| 4,159,893 | A | 7/1979 | Ham |
| 4,180,101 | A | 12/1979 | Wegge |
| 4,202,376 | A | 5/1980 | Forsell |
| 4,405,161 | A | 9/1983 | Young et al. |
| 4,444,041 | A | 4/1984 | Zison |
| 4,770,676 | A | 9/1988 | Sircar et al. |
| 4,842,060 | A | 6/1989 | Paulus |
| 4,998,585 | A | 3/1991 | Newcomer et al. |
| 5,063,519 | A | 11/1991 | Zison |
| 5,141,404 | A | 8/1992 | Newcomer et al. |
| 5,146,998 | A | 9/1992 | Cordry et al. |
| 5,147,184 | A | 9/1992 | Newcomer et al. |
| 5,147,185 | A | 9/1992 | Niehaus et al. |
| 5,211,428 | A | 5/1993 | Emerson et al. |
| 5,259,450 | A | 11/1993 | Fischer |
| 5,261,348 | A | 11/1993 | Niehaus et al. |
| 5,301,749 | A | 4/1994 | Fischer et al. |
| 5,355,739 | A | 10/1994 | Cooper et al. |
| 5,358,037 | A | 10/1994 | Edwards et al. |
| 5,358,038 | A | 10/1994 | Edwards et al. |
| 5,400,650 | A | 3/1995 | Niehaus et al. |
| 5,419,191 | A | 5/1995 | Niehaus et al. |
| 5,442,140 | A | 8/1995 | McGrane |
| 5,495,890 | A | 3/1996 | Edwards et al. |
| 5,549,157 | A | 8/1996 | Johnson et al. |
| 5,611,844 | A | 3/1997 | Troost et al. |
| 5,616,841 | A | 4/1997 | Brookshire |
| 5,695,641 | A | 12/1997 | Cosulich et al. |
| 5,701,953 | A | 12/1997 | Stecker et al. |
| 5,967,235 | A | 10/1999 | Scott |
| 6,039,546 | A | 3/2000 | Edwards et al. |
| 6,105,669 | A | 8/2000 | Davis |
| 6,169,962 | B1 | 1/2001 | Brookshire et al. |
| 6,206,657 | B1 | 3/2001 | Newcomer |
| 6,220,823 | B1 | 4/2001 | Newcomer |
| 6,224,343 | B1 | 5/2001 | Newcomer |
| 6,298,721 | B1 | 10/2001 | Schuppe et al. |
| 6,393,821 | B1 | 5/2002 | Prabhu |
| 6,418,788 | B2 | 7/2002 | Articolo |
| 6,450,784 | B2 | 9/2002 | Newcomer |
| 6,456,201 | B1 | 9/2002 | Mioduszewski et al. |
| 6,502,632 | B1 | 1/2003 | Pittman |
| 6,508,310 | B1* | 1/2003 | Mioduszewski ........ F04B 43/10 166/250.15 |
| 6,525,655 | B2 | 2/2003 | Huang |
| 6,591,695 | B1 | 7/2003 | Brookshire et al. |
| 7,007,541 | B2 | 3/2006 | Henry et al. |
| 7,231,968 | B2 | 6/2007 | Owens |
| 7,347,255 | B2 | 3/2008 | Fischer et al. |
| 7,587,940 | B2 | 9/2009 | Hewitt |
| 7,588,725 | B2 | 9/2009 | Ozbal et al. |
| 7,832,295 | B2 | 11/2010 | Rodriguez et al. |
| D644,053 | S | 8/2011 | Newcomer |
| 9,062,536 | B2 | 6/2015 | Fischer et al. |
| 9,068,421 | B2 | 6/2015 | Colby |
| D803,081 | S | 11/2017 | Scott et al. |
| 10,908,140 | B2 | 2/2021 | McKee |
| 2002/0166663 | A1 | 11/2002 | Last et al. |
| 2002/0178789 | A1 | 12/2002 | Sunshine et al. |
| 2003/0077180 | A1 | 4/2003 | Newcomer |
| 2003/0148672 | A1 | 8/2003 | Henry et al. |
| 2005/0091950 | A1 | 5/2005 | Weaver et al. |
| 2005/0103497 | A1 | 5/2005 | Gondouin |
| 2011/0203146 | A1 | 8/2011 | Newcomer |
| 2012/0024042 | A1 | 2/2012 | Vass et al. |
| 2015/0233884 | A1* | 8/2015 | Burge ................ G01N 33/1826 422/51 |
| 2016/0215774 | A1 | 7/2016 | Oklejas et al. |
| 2017/0131253 | A1 | 5/2017 | Gutierrez |
| 2017/0248514 | A1 | 8/2017 | Pavey et al. |
| 2019/0219457 | A1 | 7/2019 | Kimbell et al. |
| 2019/0271615 | A1* | 9/2019 | Trumbo ............. G01N 33/1826 |
| 2019/0335683 | A1 | 11/2019 | Kuckuck et al. |
| 2019/0369077 | A1 | 12/2019 | McKee |
| 2020/0064261 | A1 | 2/2020 | Baltz et al. |
| 2020/0086364 | A1 | 3/2020 | Spicer et al. |
| 2020/0240878 | A1 | 7/2020 | Trumbo et al. |
| 2020/0256342 | A1 | 8/2020 | Colby et al. |
| 2020/0263705 | A1 | 8/2020 | Schaupp et al. |
| 2020/0263706 | A1 | 8/2020 | Wells et al. |
| 2020/0334515 | A1 | 10/2020 | Schaupp et al. |

FOREIGN PATENT DOCUMENTS

| | | |
|---|---|---|
| WO | 9214929 A1 | 9/1992 |
| WO | 0025108 A1 | 5/2000 |
| WO | 2017111991 A1 | 6/2017 |
| WO | 2019157192 A1 | 8/2019 |

OTHER PUBLICATIONS

International Search Report and Written Opinion from PCT Application Serial No. PCT/IB2020/054394, dated Aug. 27, 2020, 18 pages.

International Search Report and Written Opinion from PCT Application Serial No. PCT/US2021/019805, dated May 26, 2021, 11 pages.

* cited by examiner

ENVIRONMENTAL GROUNDWATER SAMPLING SYSTEM

CROSS-REFERENCE TO RELATED APPLICATION(S)

This application claims the benefit of U.S. Provisional Application No. 62/981,626 filed Feb. 26, 2020, for "Environmental Ground Water Sampling System" by David B. Kaminski.

FIELD OF THE INVENTION

The present disclosure relates generally to pumping of water from a well and, in particular, to the sampling of groundwater pumped from the well and the testing of groundwater for contaminants.

BACKGROUND

Groundwater near a potential contaminated site; such as a landfill, refinery, factory, airport, and mine; can contain contaminating chemicals that can be harmful to humans, wildlife, and vegetation. Thus, it is important to monitor the possibility of contaminants in the groundwater near those sites. To monitor the groundwater, numerous wells are constructed surrounding the sites, and groundwater is regularly removed and tested to confirm the existence or absence of contaminants in the groundwater.

SUMMARY

A system for sampling groundwater from a well that includes a pump configured to be at least partially submerged in the groundwater within the well and pump the groundwater out of the well, a sensor configured to output a signal indicative of the depth of the groundwater in the well, and a controller in communication with the sensor. The controller is configured to receive the signal indicative of the depth of the groundwater from the sensor and compensate for groundwater ingress into the well by adjusting a rate of flow of groundwater pumped by the pump based on the signal to stabilize the depth of groundwater in the well while the pump is pumping groundwater from the well.

A method of collecting a sample of groundwater from a well that includes operating a pump in the well at a flow rate to remove groundwater from the well, repeatedly measuring a depth of the groundwater in the well and communicating signals indicative of the depth of the groundwater to a controller, adjusting the flow rate of the pump by the controller based on the signals indicative of the depth of the groundwater, and collecting the sample of the groundwater when the depth of the groundwater is stable. The controller decreases the flow rate of the pump if the depth of the groundwater is decreasing and increases the flow rate of the pump if the depth of the groundwater is increasing to compensate for ingress of groundwater into the well.

DETAILED DESCRIPTION

Figure 1:
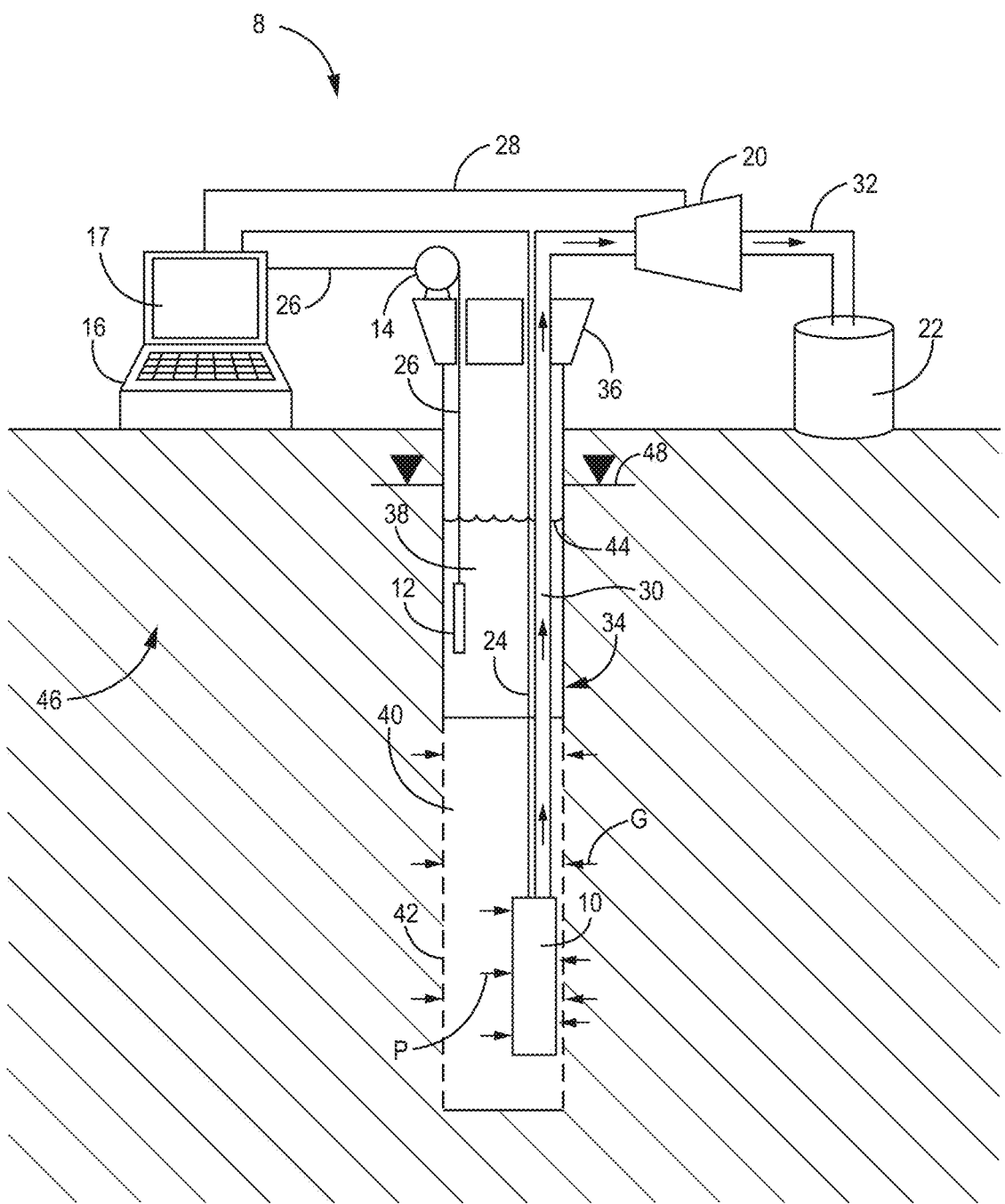
FIG. 1 is a groundwater sampling system in a well located in an aquifer.

A system and method for removing/extracting groundwater from a well and sampling the groundwater to test for contaminants is disclosed herein. The system includes a pump at least partially submerged in the groundwater in the well for pumping the groundwater out of the well and a sensor in the well for measuring a depth of the groundwater in the well. The system also includes a controller that can have a computer processor with the controller being in communication with the pump and the sensor. The controller instructs the pump to increase a pump/flow rate or decrease a pump/flow rate depending on the depth of groundwater in the well as indicated by the sensor. The controller can control the flow rate of the pump such that the amount of groundwater removed from the well can be equal to the amount of groundwater flowing into the well from the surrounding aquifer/ground, thus creating a water column in the well that is at a stable depth.

A water column with a stable depth during removal of groundwater from the well for testing is important because, to get an accurate sample of groundwater that represents the state of the groundwater in the surrounding aquifer/ground, the sample of groundwater should be pulled from groundwater that was recently within the surrounding aquifer/ground, not groundwater that has sat stagnant in the well. When the groundwater in the well is being pumped out at a flow rate that produces a stable depth of water within the well, the groundwater near a top of the well, in a stagnant water zone/column, stays relatively stationary and does not flow into the pump to become part of the sample of groundwater to be tested. Rather, the water pumped from the well and becomes the sample of groundwater to be tested is in a screened, flow zone below the stagnant water zone/column. The groundwater in the flow zone is free to flow into and out of the well from and to the surrounding aquifer, thus making the groundwater in the flow zone an accurate representation of the overall state of the groundwater in the aquifer (and thus making the groundwater pumped from the flow zone an accurate sample for testing).

Prior to the disclosed system and method, the entirety of the groundwater in the well would have to be pumped out before a sample of the groundwater could be collected. Because the groundwater removed from the well may contain contaminants, the removed groundwater must be treated as hazardous and go through water treatment. Thus, it is advantageous to reduce the amount of groundwater removed from the well during the sampling and testing process. The disclosed system and method reduce the amount of groundwater that needs to be removed from the well during the sampling and testing process because the flow into the pump is stable (i.e., the flow into the pump is equal to the flow into the well from the surrounding aquifer/ground) such that the water in the stagnant water zone does not flow into the flow zone (and then into the pump) to taint the sample of groundwater. The controller is configured to automatically adjust the flow rate of the pump to accomplish a stable state by receiving signals indicative of the depth of the groundwater in the well and adjusting the flow rate off the pump accordingly. For example, as will be detailed below, if the depth of groundwater in the well is decreasing (as indicated by the sensor), the controller will instruct the pump (or adjust the power/energy to the pump) to reduce the flow rate of groundwater being pumped out of the well by the pump.

These and other features of the disclosed system and method will be realized in the subsequent disclosure.

Figure 2:
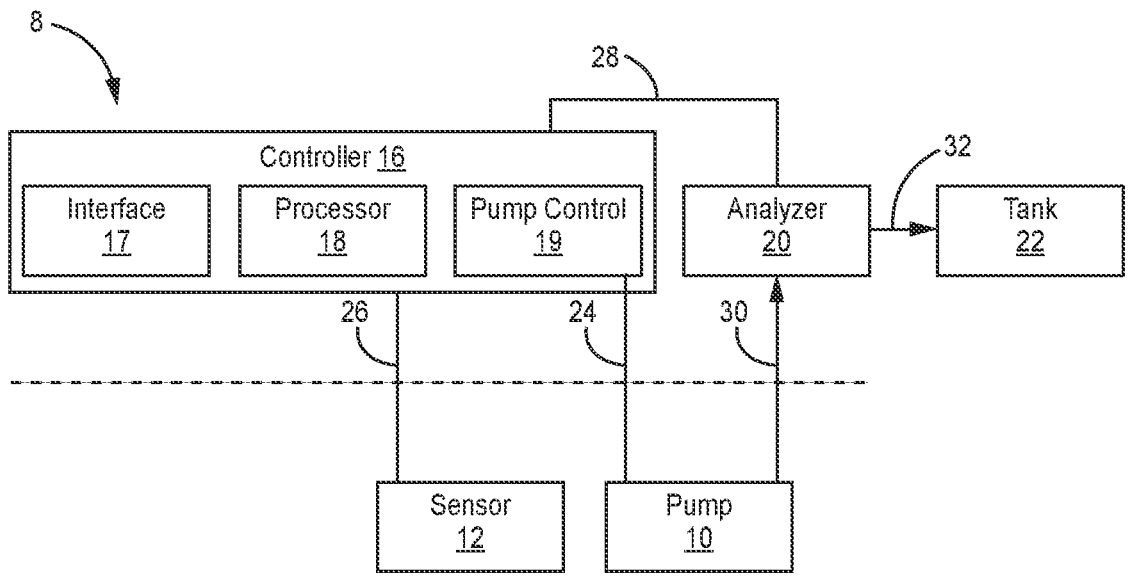
FIG. 2 is a schematic of the groundwater sampling system.

FIG. 1 is a groundwater sampling system positioned in/adjacent a well, and FIG. 2 is a schematic of the groundwater sampling system. Groundwater sampling system 8 includes pump 10 (with groundwater flowing into pump 10 designated as pump inflow P), sensor 12, sensor reel 14, controller 16 (having interface 17, processor 18, and pump control 19), analyzer 20, and tank 22. Groundwater sampling system 8 also includes pump communication (and/or power line) 24 extending between pump 10 and controller 16, sensor communication line 26 extending between sensor 12 and one or both of sensor reel 14 and controller 16, analyzer communication line 28 extending between controller 16 and analyzer 20, groundwater line 30 that conveys groundwater from pump 10 to analyzer 20, and analyzer outlet line 32 that conveys groundwater from analyzer 20 to tank 22. FIG. 1 also shows well 34, which includes cap 36, stagnant water column/zone 38, flow zone 40, screen 42, and water surface 44. Well 34 is located within aquifer/ground 46, which includes water table level 48 (with groundwater flowing into well 34 from aquifer 46 designated as groundwater inflow G).

Well 34 is located (e.g., drilled) in aquifer/ground 46. This disclosure will use aquifer 46 and ground 46 interchangeably because ground 46 can include an aquifer such that ground 46 contains and can transmit groundwater. While ground 46 in this disclosure contains an aquifer with water table level 48 (the level in ground 46 at which the groundwater is located), well 34 and groundwater sampling system 8 can be located in ground 46 that does not contain an aquifer but otherwise is able to fill at least a portion of well 34 with groundwater. Ground 46 can comprise permeable rock, sand, silt, clay, combinations thereof, or any type of material. While shown near the surface of ground 46, water table level 48 can be deep underground (e.g., fifty feet or more from the surface of ground 46) or very close to the surface of ground 46 (e.g., one foot or less from the surface of ground 46). The location of water table level 48 is dependent upon numerous factors, including the type of material forming ground 46, environmental/weather/climate conditions around well 34, and others. As is typical with an aquifer, ground/aquifer 46 can include groundwater that flows horizontally and/or vertically within ground 46.

Well 34 can be drilled or otherwise constructed in ground 46 and is typically a cylindrical cavity within which water can pool. Well 34 can have any depth necessary to allow for the pooling and collecting of groundwater within well 34. However, well 34 should be at least deeper than water table level 48 is from the surface of ground 46 to allow for groundwater to flow into well 34 (so that the groundwater can be collected and removed for sampling). Well 34 can be vertical or angled, can be straight or have curves or other nonlinear features, and/or can have any diameter that provides sufficient space for pump 10, sensor 12, and the collection of groundwater. For example, well 34 as disclosed in FIG. 1 can be two to four inches (5-10 centimeters) in diameter and extends straight vertically downward.

Cap 36 is at a top of well 34 and provides a cover to well 34. Cap 36 can be removable and/or can include orifices that allow for the insertion and removal of sensor 12, pump 10, and/or other components into well during the collection of groundwater by groundwater sampling system 8. Cap 36 can be threadedly attached or otherwise fastened to the top of well 34. Well 34 does not need to include cap 36 and can have well 34 open to the environment.

Well 34 includes walls that provide structural support to well 34 to ensure well 34 does not collapse inward. The walls of well 34 can be constructed from a variety of materials, such as PVC pipe, concrete, metal, or another material. Near a bottom of well 34, the walls can be porous, such as screen 42, that allow water to flow into (and out of) well 34 from (and to) aquifer 46. While described as a screen, screen 42 can have any configuration that allows for groundwater to flow into and out of well 34 while also preventing well 34 from collapsing or otherwise becoming filled with material from ground 46. Some configurations of well 34 may include screen 42 that extends above water table level 48 or well 34 that does not include screen 42.

Well 34 in FIG. 1 is shown as being divided into two zones distinguished by the capability of groundwater to flow through and within those zones. Near the top of well 34 and extending between water table level 48 of aquifer 46 and the top of screen 42 (as shown by a horizontal line in FIG. 1) is stagnant water column/zone 38. The walls surrounding stagnant water column/zone 38 are not porous and allow minimum flow of groundwater into and out of stagnant water zone 38 directly from and to aquifer 46. Thus, groundwater within stagnant water zone 38 is stagnant and does not flow out of well 34. Because the groundwater within stagnant water zone 38 does not flow into and out of aquifer 46 and instead remains within well 34, the groundwater in the stagnant water zone 38 is not an accurate representation of groundwater within aquifer 46. Rather, the groundwater within stagnant water zone 38 can have a higher or lower level of contaminants and thus spoil the testing (i.e., result in an inaccurate reading) of the contaminants in the groundwater of aquifer 46 by analyzer 20. Between stagnant water zone 38 and a bottom of well 34 is flow zone 40, which can be surrounded by walls formed by screen 42. Flow zone 40 is configured to allow groundwater from aquifer 46 to flow into well 34 and to allow groundwater within flow zone 40 to flow out of well 34 into aquifer 46. Because groundwater within flow zone 40 is continuously flowing into and out of aquifer 46, the groundwater in flow zone 40 is a more accurate representation of the groundwater within aquifer 46 and thus is a better sample for testing by analyzer 20.

In FIG. 1, the groundwater within well 34 has water surface 44 at the top of stagnant water zone 38. As will be discussed below, water surface 44 in well 34 is lower than water table level 48 of aquifer/ground 46 because pump inflow P into pump 10 is or was greater than groundwater inflow G into well 34. When pump 10 is not in operation, water surface 44 will typically be equal to water table level 48. The level of water surface 44 can depend on several factors, such as the height of water table level 48 and the hydraulic pressure surrounding well 34.

As mentioned above, groundwater sampling system 8 collects/removes groundwater from flow zone 40 for testing by analyzer 20 without removing any groundwater present in stagnant water zone 38 (thus preventing the groundwater within stagnant water zone 38 from skewing/spoiling the accuracy/results of the testing of the groundwater representative of the groundwater in aquifer/ground 46). This is accomplished by equaling pump inflow P rate of groundwater into pump 10 from well 34 to groundwater inflow G rate into well 34 from ground 46. When this stability is present, the groundwater level within flow zone 40 is constant and the groundwater within stagnant water zone 38 does not flow or otherwise move into flow zone 40 (so water level 44 is not rising or falling).

Pump 10 can be positioned within flow zone 40 of well 34 and is configured to pump/remove groundwater from well 34 and convey the groundwater to analyzer 20 and tank 22 via groundwater line 30 and analyzer outlet line 32, respectively. Pump 10 can be any type of pump configured to pump water, such as a pneumatically operated pump (e.g., a bladder pump), an electrically powered pump (e.g., having a turbine or alternatively a positive displacement mechanism such as a piston), and/or a peristaltic type pump. Pump 10 can be in communication with controller 16 via pump communication/power line 24 such that controller 16 is able to control the flow rate of pumping/removing (i.e., pump inflow P rate) of groundwater from well 34 by pump 10. Pump 10 should be able to vary the speed/flow rate at which groundwater is removed from well 34. For example, if pump 10 is an electrically powered pump or a peristaltic pump, the flow rate of groundwater removed from well 34 by pump 10 can be varied by altering the speed of the motor of pump 10 to either reduce the speed (which, in turn, reduces the amount of groundwater pumped by pump 10) or increase the speed (which, in turn, increases the amount of groundwater pumped by pump 10). For a pneumatically operated pump, such as a bladder pump, the flow rate of groundwater removed from well 34 by pump 10 can be varied by altering the pressure of the gas provided to pump 10 and/or by altering the duration of the pump cycle (i.e., the time it takes for the pump to complete one cycle of filling the pump with water, pushing the water out of the pump through the use of pressurized gas, and then venting the pressurized gas to allow for the pump to fill with water again to repeat the cycle). To increase the speed/flow rate of a pneumatically operated pump, the pressure of the gas provided to pump 10 can be increased and/or the duration of the pump cycle can be decreased. Alternately, to decrease the speed/flow rate of the pneumatically operated pump, the pressure of the gas provided to pump 10 can be decreased and/or the duration of the pump cycle can be increased.

The control of pump 10 by pump control 19 of controller 16 can be via wireless or wired communication of control signals to pump 10 or another type of communication, such as by controlling the amount/level of power transmitted to pump 10 via pump communication/power line 24. For example, in the case of a pneumatically operated pump 10, pressurized air (or another gas) may be supplied from controller 16 (or controller 16 can control the amount of air supplied from an air reservoir) through a hose to pump 10. As such, controller 16 may provide and/or include a reservoir of pressurized air to supply to pump 10 for powering pump 10 with the pressurized air being supplied, for example, via a tank or generated onsite by a compressor. The amount of pressurized air provided to pump 10 can control the speed at which pump 10 operates, with more pressurized air provided resulting in an increase in pump inflow G rate and less pressurized air provided resulting in a decrease in pump inflow G rate. In another example, in the case of an electrically powered pump 10, electricity may be provided from controller 16 (e.g., by a battery, generator, and/or electrical grid connection) through power line 24 to pump 10. The amount of electricity provided to pump 10 can control the speed at which pump 10 operates, with more electricity provided resulting in an increase in pump inflow G rate and less electricity provided resulting in a decrease in pump inflow G rate. In another example, pump 10 may operate on a constant supply of power (e.g., pneumatic or electric) while pump inflow P rate (i.e., the rate of pumping of water by pump 10) is controlled based on control signals sent to pump 10 by pump control 19.

Pump 10 conveys/pumps groundwater to analyzer 20 and/or tank 22 via groundwater line 30 and analyzer outlet line 32. Analyzer 20 and tank 22 can be located above ground such that pump 10 expels groundwater from well 34 via groundwater line 30. Thus, pump 10 is at least partially submerged in the groundwater in well 34. Pump 10 can be supported by one or more tethers (or other components), which can provide support as well as supply power to pump 10. As such, the tethers can be pump communication/power line 24. Groundwater line 30 can have any size, shape, and configuration to allow for groundwater to flow from pump 10 to analyzer 20. If analyzer 20 is not collecting a sample of the groundwater for testing, the groundwater pumped by pump 10 can bypass or flow straight through analyzer 20 to analyzer outlet line 32 and then to tank 22. Groundwater line 30 can continuously extend between pump 10 and analyzer 20, or if analyzer 20 is removable from a location adjacent well 34, groundwater line 30 can have a connector such that a portion of groundwater line 30 within well 34 is stationary and a portion of groundwater line 30 outside well 34 is moveable. For example, a technician testing the groundwater in aquifer/ground 46 can arrive on site at well 34 with analyzer 20 and tank 22 (with analyzer outlet line 32 therebetween) located in the technician's vehicle, connect analyzer 20 to a portion or an end of groundwater line 30, and begin operation of pump 10 to convey the groundwater to analyzer 20 (and eventually to tank 22).

Sensor 12 is a measurement device/sensor configured to determine the depth of groundwater in well 34 and transmit that information to controller 16 via sensor communication line 28. Sensor 12 can transmit a signal indicative of the depth of the groundwater in well 34 to controller 16. The depth of groundwater 34 can be continuously or incrementally measured/determined by sensor 12 and continuously or incrementally conveyed to controller 16. For example, sensor 12 can measure and transmit the depth of groundwater in well 34 to controller 16 multiple times per second or once every 1, 5, 10, or 15 seconds. Sensor 12 can be any type of measurement device able to determine the depth of groundwater in well 34, such as a pressure transducer that is submerged in the groundwater to measure a change in pressure at a constant location within well 34, an ultrasonic device that measures the change in the level/location of water surface 44, any type of probe, or a sonar device that measures the depth of the groundwater. Sensor 12 can be located within the groundwater in stagnant water zone 38 or flow zone 40, can be located between water surface 44 and the top of well 34, or can be at another location, such as within well 34 but not in contact with the groundwater.

The term "depth" as used herein refers to the height of the liquid column from the bottom of well 34 to water surface 44. For a given sized well and/or reservoir, greater volume of water will have a greater depth while lesser volume of water will have a lesser depth. Sometimes in the industry, the term "depth" refers to the distance from the top of well 34 (at cap 36 and/or at the ground surface) down to water surface 44. While the two uses of the term are generally equivalent, they are also reciprocal. For example, increasing water column height corresponds with decreasing distance from the top of well 34 to water surface 44 while decreasing water column height corresponds with increasing distance from the top of well 34 to water surface 44. Due to the two meanings being reciprocal, the meaning of "depth" referring to distance from the top of well 34 to water surface 44 could be substituted herein, although the terms "greater/lesser" and "increasing/decreasing" regarding depth as used herein should be switched.

Sensor 12 is connected to sensor communication line 26, which, in addition to conveying information to and from sensor 12, can be a tether to provide support to sensor 12 to allow for sensor to be insertable into and removable from well 34. Sensor reel 14 can be along sensor communication line 26. Sensor communication line 26 can wind and unwind around sensor reel 14 to insert and remove sensor 12 from well 34. If sensor 12 is not removable (or removal is not desired) from well 34, sensor reel 14 may not be present in groundwater sampling system 8. Additionally, while shown as a cylindrical drum onto which sensor communication line 26 can wind, sensor reel 14 can have another configuration. Sensor reel 14 can be located on cap 36 (as shown in FIG. 1) or at another location, such as adjacent controller 16 and/or distant from well 34. Sensor 12 and/or sensor reel 14 can be in wired or wireless communication with controller 16 to transmit information/data regarding the depth of groundwater in well 34 from sensor 12 to controller 16 (and/or processor 18 of controller 16) and/or to receive commands from controller 16. Additionally, sensor 12 can receive power from controller 16, or sensor 12 can have its own power source, such as a battery. If sensor 12 is positioned within the groundwater in well 34, sensor 12 may need to be washed off after removal as the groundwater within well 34 may be contaminated and need to be treated as a hazardous material.

Controller 16 can include interface 17, processor 18 (or multiple processors), and pump control 19. Controller 16 is configured to adjust pump 10 and pump inflow P to equal groundwater inflow G to stabilize water surface 44 in well 34. In other words, controller 16 is configured to adjust the speed of pump 10 to alter the flow rate of groundwater into pump 10 (and out of well 34) to match the flow rate of groundwater into well 34 so that the amount of water within well 34 is constant to prevent water within stagnant water zone 38 from flowing into flow zone 40 and then into pump 10. If the groundwater from stagnant water zone 38 were to flow into pump 10 and be tested by analyzer 20, the test would return results that were not representative of the contaminants within aquifer 46. Thus, ideally, pump 10 pulls as little groundwater from stagnant water zone 38 as possible. This is because stagnant water zone 38 is not considered reliable for testing of the groundwater because of the greater likelihood of the water within stagnant water zone 38 containing a different chemical profile (e.g., typically having lower chemical concentrations due to diffusion of the chemicals and aerobic degradation out of the groundwater in the stagnant water zone 38) than the groundwater in the surrounding aquifer/ground 46 that has flowed into flow zone 40 in well 34. Thus, it is important that controller 16 adjust pump 10 so that the flow rate of water removed from well 34 is equal to the flow rate of water coming into flow zone 40 of well 34. If water from stagnant water zone 38 is pumped by pump 10, then that water has to be flushed/purged to tank 22 before a sample of the groundwater from aquifer 46 can be collected and tested. While the entire stagnant water zone 38 could be pumped out before sampling, such a process would be laborious, time consuming, costly (as the groundwater removed must be treated as a hazardous material), and complicated by the constant inrush of groundwater into well 34 from aquifer 46 to replace the groundwater removed from well 34.

Controller 16 can be a single apparatus or can be a set of distributed apparatuses that include interface 17, processor 18, and/or control pump 19. While controller 16 will generally be discussed as a single apparatus, it will be understood that each of the components and functions referenced herein can be embodied as a separate apparatus that is part of controller 16 and performs the functions described herein.

Controller 16 can include one or multiple processors 18 configured to execute steps of a software program to adjust the speed/pump rate of pump 10 in response to information/data/signals received from sensor 12. Processor 18 can be a microprocessor or other types of logic circuitry that can execute logic programming to perform functions. Processor 18 can include memory that stores program instructions executable by the logic circuitry to perform the functions described herein. Processor 18 can be a single chip, a plurality of chips, and/or other types of logic circuitry. Processor 18 can execute other commands and/or tasks, such as commands from the technician as entered via interface 17, and/or transmit instructions to analyzer 20 to start or end the collection of samples of groundwater for testing. Additionally, controller 16 and/or processor 18 can receive and process information from pump 10, sensor 12, and analyzer 20 and instruct interface 17 to display the information. Controller 16 and/or processor 18 can include other features and functionalities not expressly mentioned herein.

Controller 16 can be mobile such that a technician testing the groundwater in aquifer/ground 46 can arrive on site at well 34 with controller 16 in a carrying case or in the technician's vehicle, connect (wired or wirelessly) to pump 10 and/or the other components of groundwater sampling system 8, and begin the process of collecting and testing the groundwater.

Interface 17 can be part of controller 16 or can be a separate apparatus that is in wired or wireless communication with controller 16. Interface 17 can be used to display and/or otherwise provide information to a user, such as a technician. Interface 17 can also receive commands from a user and route such commands to controller 16. Interface 17 can include one or more of a display, touchscreen, button dials, touchpads, keyboard, or other type of input and/or output.

Controller 16 can include pump control 19, which can transmit instructions to pump 10 to increase or decrease pump inflow P rate. In one example, pump control 19 can be a pneumatic supply having a regulator for outputting a pressurized gas at a controlled pressure and/or flow rate to pump 10 for adjusting the pump/flow rate of groundwater into pump 10 (and thus out of well 34). In another example, if pump 10 is an electric pump, pump control 19 can change the power of a signal output from controller 16 and supplied to pump 10 to change the pump inflow P rate of pump 10. Processor 18 can instruct pump control 19 to adjust the power/pressurized air provided to pump 10, or pump control 19 can adjust the flow rate of pump 10.

Controller 16 can be configured to continuously or periodically receive information (e.g., signals) from sensor 12 regarding the depth of groundwater in well 34 and instruct pump 10 (e.g., by adjusting pressurized air, electricity, etc. to pump 10) to increase or decrease pump inflow P rate to remove groundwater from well 34 at a greater or lesser rate. Controller 16 can be configured to change the level of power supplied to pump 10 in proportion to the rate of change of depth of the groundwater in well 34 such that controller 16 reduces the power supplied to pump 10 a greater amount when the rate of change of depth of the groundwater is relatively high and reduces the power supplied to pump 10 a lesser amount when the rate of change of depth of the groundwater in well 34 is relatively low. For example, if sensor 12 transmits signals to controller 16 that are indicative of the depth of groundwater in well 34 decreasing rapidly (pump 10 is removing groundwater from well 34 at a much greater rate than groundwater inflow G), controller 16 can adjust pump 10 to decrease pump inflow P at a rate that is greater than if the depth of groundwater in well 34 was decreasing slowly. Additionally, if sensor 12 transmits signals to controller 16 that are indicated of the depth of groundwater in well 34 increasing rapidly (groundwater inflow G is much greater than the rate at which pump 10 is removing water from well 34), controller 16 can adjust pump 10 to increase pump inflow P at a rate that is greater than if the depth of groundwater in well 34 was increasing slowly. It should be noted that the level of groundwater in well 34 cannot rise above water table level 48, so for the depth of groundwater in well 34 to increase, the depth of groundwater in well 34 would have first needed to be drawn down such that water surface 44 is below water table level 48.

Adjusting the rate of pumping of pump 10 by controller 16 depending on the information received from sensor 12 can be performed automatically by controller 16 without input from a user. Additionally, with controller 16 and many components of groundwater sampling system 8 able to be moved and utilized at multiple wells for collecting samples and testing groundwater at different locations, controller 16 can store data and operational parameters specific to each well. For example, the maximum groundwater inflow G rate for each well can vary substantially, so the maximum pump inflow P rate at which pump 10 can operate will also vary. Controller 16 can be configured to store this data and ensure that pump 10 at each respective well does not operate above that maximum rate. Additionally, controller 16 can store and utilize other data, such as the volume of flow zone 40, which may be important as the volume of groundwater equal to the volume of flow zone 40 may be desired to be pumped out before the collection and testing of groundwater by analyzer 20 begins.

The variation of groundwater inflow G rates of different wells can be large. Some wells have large and rapid inrush of groundwater to replace any groundwater removed from the well, while others have a very slow refill rate. Without groundwater sampling system 8, a user/technician would have substantial difficulty attempting to reach a pump outflow rate of pump 10 (e.g., pump inflow P rate) that stabilizes the depth of the groundwater in well 34.

Analyzer 20 can be a multi-parameter water quality measurement system configured to measure the groundwater from aquifer/ground 46 for indicator parameters, which are relative indicators of changing water quality. For example, analyzer 20 can have one or more chemical analysis sensors configured to test for the presence and/or concentration of one or more chemicals in the groundwater outputted by pump 10. Analyzer 20 can include a sonde and flow cell that allow for continual measurement and analysis of selected water quality parameters (e.g., indicator parameters). Analyzer 20 can analyze in real time and output and/or store the resultant data, and additionally may store one or more samples of the groundwater in one or multiple containers for later laboratory testing, either on site or at an offsite laboratory. While analyzer 20 is shown as being above ground in FIG. 1, analyzer 20 may be located within the well. Analyzer 20 can continuously or periodically measure the groundwater for indicator parameters and/or contaminants anytime pump 10 is removing water from well 34 and pumping it through analyzer 20. In some embodiments, analyzer 20 continuously or periodically measures the groundwater until the various indicator parameters levels in the groundwater become stable (relatively unchanged over time), which would indicate that the groundwater being removed from well 34 is an accurate representation of the groundwater in aquifer 46. After the indicator parameter levels/readings are stable (and possibly the level of groundwater in well 34 is stable), analyzer 20 can collect a sample of the groundwater for analysis.

Sampling of the groundwater should not be performed until the indicator parameters have stabilized, which can occur after flow zone 40 is purged (i.e., the volume of groundwater equal to the volume of flow zone 40 is removed from well 34). When stabilization of the indicator parameters is achieved based on selected criteria selected, controller 16 can determine that purging has been completed and can either indicate to the user/technician that sample collection and testing can begin (possibly via interface 17) and wait for the user/technician to instruct analyzer 20 to begin collection, or controller 16 can begin collecting the sample without user intervention. The signal to the user/technician can be visual (e.g., an LED or LCD indicator), audible (e.g., a buzzer or speaker on controller 16), and/or a wireless communication from controller 16 to a tablet or smartphone device (e.g., an SMS or on-scree notification) or other type of interface. As mentioned above, analyzer 20 can be mobile such that user/technician transports one analyzer 20 from one well to another for use in groundwater sampling system 8, with analyzer 20 being attachable to groundwater line 30 to receive groundwater from pump 10.

An efficient sampling protocol aims to pump/remove the sample groundwater from flow zone 40 while leaving the above water in stagnant water zone 38 in place. A user/technician can have confidence that the sample groundwater comes fresh from aquifer 46 (after that groundwater recently flowed into flow zone 40) and is unlikely to have mixed with water in the stagnant water zone 38, if pump 10 is continuously operating at a steady rate such that pump inflow P matches groundwater inflow G to produce water surface 44 that is stable (e.g., the depth of the groundwater in well 34 is not rising or lowering). In this stable state, the flow rate from aquifer 46 into well 34 (i.e., groundwater inflow G rate) is equal to the outflow rate from pump 10 (i.e., pump inflow P rate) such that the groundwater sample collected during this state is presumed to be an accurate representation of the groundwater present within aquifer 46 near well 34.

Figure 3:
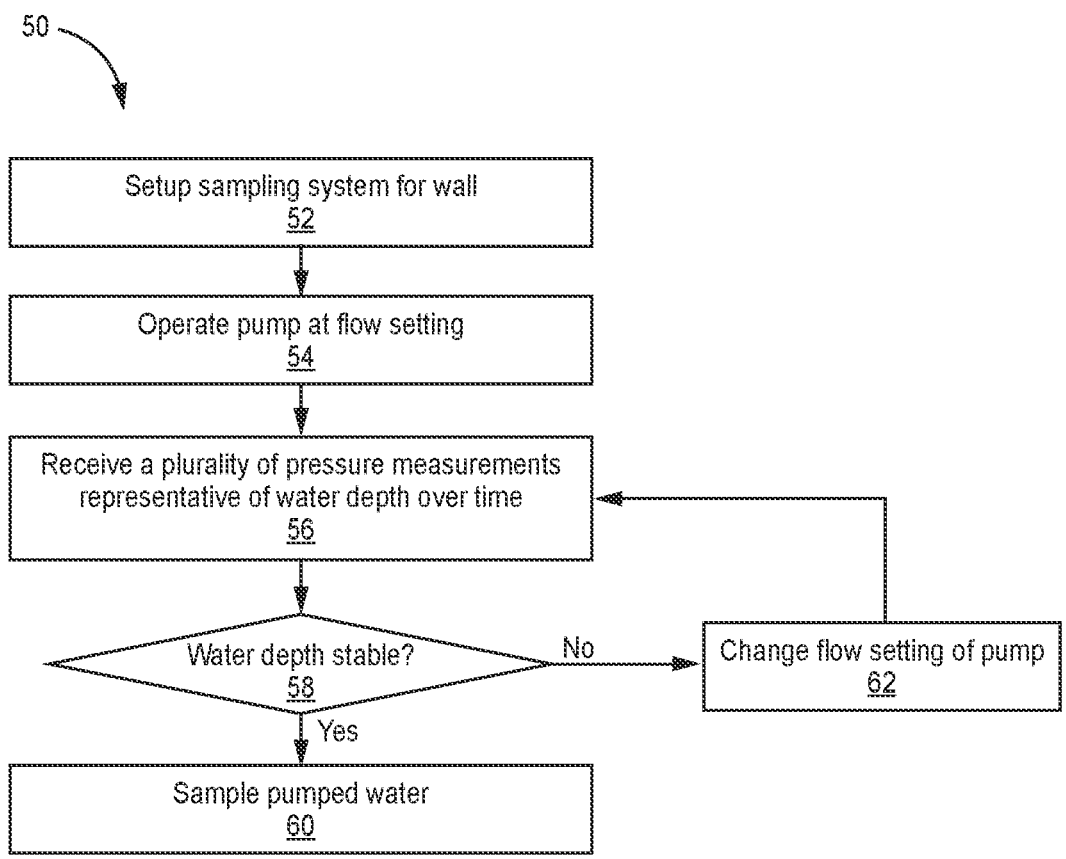
FIG. 3 is a flow chart showing a method of collecting a sample of groundwater from a well.

FIG. 3 is a flow chart showing method 50 of collecting a sample of groundwater from a well. While method 50 is disclosed herein with steps 52-62, Method 50 of collecting samples of groundwater from wells can include additional steps not expressly discussed in this disclosure, or method 50 can include fewer steps than those detailed here as all steps may not be necessary for all situations.

First, method 50 includes setting up the groundwater sampling system for the well 52. If groundwater sampling is intended to be performed multiple times as separate intervals, step 52 may need to be performed only once after the well has been constructed with all of the components being left in place near the well for the next sampling cycle. However, as disclosed above, many of the components of the groundwater sampling system can be moveable and often times will be brought out to the well site by the user/technician before the sampling cycle and taken with the user/technician after the sampling is completed. Thus, step 52 can include setting up and connecting the components to one another in a fashion similar to that shown in FIG. 1 and explained in the above disclosure. However, other alternative setups are possible.

After setting up the groundwater sampling system 52, step 54 is operating the pump at an initial flow setting. The initial flow setting can be controlled by the pump control in the controller. As discussed above, the flow setting can correspond to the power level delivered to the pump by the controller, which causes the pump to pump/remove groundwater at an output flow rate. Generally, greater power translates to a greater output flow rate and lesser power translates to a lesser output flow rate. The initial flow setting can be a default flow setting input by the user/technician, or the initial flow setting can be a flow setting used in a previous sampling cycle of the well that is saved by the groundwater sampling system/controller for use in subsequent sampling processes of that well.

Then, method 50 includes receiving information indicative of the groundwater depth 56. The sensor can be used to measure the depth of the groundwater in the well. The information provided to the controller (i.e., received by the controller) can be a number representative of the depth of the groundwater, a pressure measurement that details the pressure experienced by the sensor (which, when compared to a previous measurement, can reflect whether the depth of the groundwater has increased or decreased), or another measurement. Step 56 can include multiple measurements representative of the groundwater depth over time. If the sensor is a pressure transducer, greater water depths will produce a higher pressure measurement and lesser water depths will produce a lower pressure measurement. Logic circuitry of the controller (e.g., the processor in the controller) can use a mathematical function, index, or another process to map the information (e.g., signals) output from the sensor to convert the information to water depth values. In another example, the logic circuitry in the controller can merely use relative changes in the measurements/signals output from the sensor to assess relative changes in the water depth without converting the information into water depth values.

Upon the initiation of step 54 (operating the pump at the initial flow setting), the depth of the groundwater in the well will drop such that the water surface in the well will be below the water table level in the aquifer/ground. Because of the pressure differential created by the removal/pumping of groundwater out of the well, a groundwater inflow into the well from the aquifer/ground will occur. The depth of the groundwater in the well is measured over time to determine if the depth is decreasing, increasing, or stable. Monitoring the change in depth of the groundwater in the well is important in assessing whether the depth is stable, which is the goal before collecting and testing of the groundwater is performed. A stable depth of the groundwater corresponds to an equalization between the pump inflow, which removes the water from the well, and the groundwater inflow, which introduces water into the well from the aquifer/ground.

After receiving information indicative of the groundwater depth 56, the controller determines if the groundwater depth is stable 58. This determination is made with information of the groundwater depth, and can be performed by comparing the most recent water depth information to the previous water depth information. A stable depth of the groundwater in the well will return depth information that is similar from one measurement to the next (e.g., the pressure measurement by the sensor is constant). For example, if the sensor outputs (and the controller receives) three consecutive indications that the depth of the groundwater in the well has not changed, then the depth can be determined to be stable.

If the depth of the groundwater is determined to be stable in step 58, the next step is to collect a sample of the groundwater 60, which can also include testing the groundwater for contaminants. Step 60 can be performed by the analyzer or another water quality testing apparatus/system. Sampling/testing the groundwater 60 can include chemically testing the groundwater in real time via the analyzer and/or capturing a volume of the groundwater in a container for later testing in a laboratory. As detailed above, the controller can be in communication with the analyzer and send instructions, such as a signal, to the analyzer to automatically initiate the sampling or any type of testing of step 60 based on the determination in step 58 that the depth of the groundwater in the well is stable. Method 50 can end after step 58, in which case the pump ceases operation and the moveable components of the groundwater sampling system can be packed up and transported to another well for another groundwater sampling process.

If the depth of the groundwater is determine to be unstable/changing (which will typically be the case during the first number of iterations of steps 56 and 58), then step 62 is performed in which the flow setting of the pump is adjusted and steps 56 (receiving information of the groundwater depth) and 58 (determining if the groundwater depth is stable) are repeated until the groundwater depth is determined to be stable and sampling/testing of the groundwater is performed 60.

The flow setting of the pump corresponds to the flow/removal of groundwater from the well, and the adjusting/altering/changing of the flow setting of the pump can be performed by changing the power delivered/supplied to the pump by the controller (e.g., from the pump control), such as pneumatic or electrical power. The change in flow setting of the pump 62 is based on the information/measurements collected in step 56, and can be based on a change between the plurality of measurements. For example, the amount of the decrease in the flow setting of the pump (and thus the flow of groundwater out through the pump) can be based on a trend of the plurality measurements showing a decrease in the depth of the groundwater in the well. The amount of decrease of the flow setting can be proportional to the degree of decrease in the plurality of measurements indicative of the depth of the groundwater in the well. If the degree of decrease in the plurality of measurements is at a relatively large rate (i.e., the depth of the groundwater is decreasing quickly), than the amount of decrease of the flow setting can be relatively large to bring the depth of the groundwater closer to stability. But if the depth is determined to be decreasing at a relatively low rate, than the amount of decrease of the flow setting (i.e., the pumping of the groundwater out of the well) can be relatively small.

The amount of change/adjustment in the flow setting 62 (i.e., the pumping rate of the pump) can be proportional to the rate of change (i.e., the rate of increase or decrease) of the depth of the groundwater in the well to efficiently arrive at a stable depth of water while minimizing the risk that the adjustment overshoots the pump/flow rate that results in a stable depth of groundwater, thereby decreasing the amount of groundwater that needs to be removed/pumped from the well before a sample can be collected. For example, if the depth of the water level is rapidly increasing, then a large increase in the flow output of the pump (i.e., the rate at which the pump is removing groundwater from the well) is needed to slow down the rate of the increase in the depth of the groundwater. Then, when the rate of the increase of the depth of the groundwater becomes lower, the increase in the flow setting of the pump is correspondingly lower to get the depth of the groundwater to be closer to a stable depth. A mathematical function, index, or another process can be used to translate the rate of change in the depth of groundwater in the well to the amount of change/adjustment in the flow setting of the pump. For example, the relationship between the rate of change in the depth of the groundwater and the amount of change in the flow setting of the pump can be linear.

The ability of method 50 to change the flow rate output by the pump in proportion to the rate of change of the depth of the groundwater in the well allows for method 50 to begin the process with a high flow rate of the pump (i.e., a high rate of pumping) and then quickly adjust the flow rate of the pump if the initial flow rate is too high or too low.

After the flow setting of the pump is adjusted 62, method 50 can repeat steps 56 and 58 with the plurality of groundwater depth measurements being collected while pumping at the new flow setting to determine if the depth of the groundwater in the well is stable. If the depth of the groundwater in the well is not stable, then the flow setting of the pump can be adjusted again (i.e., step 62 is repeated) and steps 56 and 58 are repeated. Method 50 can loop through these steps multiple times, adjusting the flow rate of the pump as the depth of the groundwater in the well approaches stability (as indicated by the measurements of the depth of the groundwater) until the depth is stable and collection of the sample groundwater can be performed 60.

Figure 4:
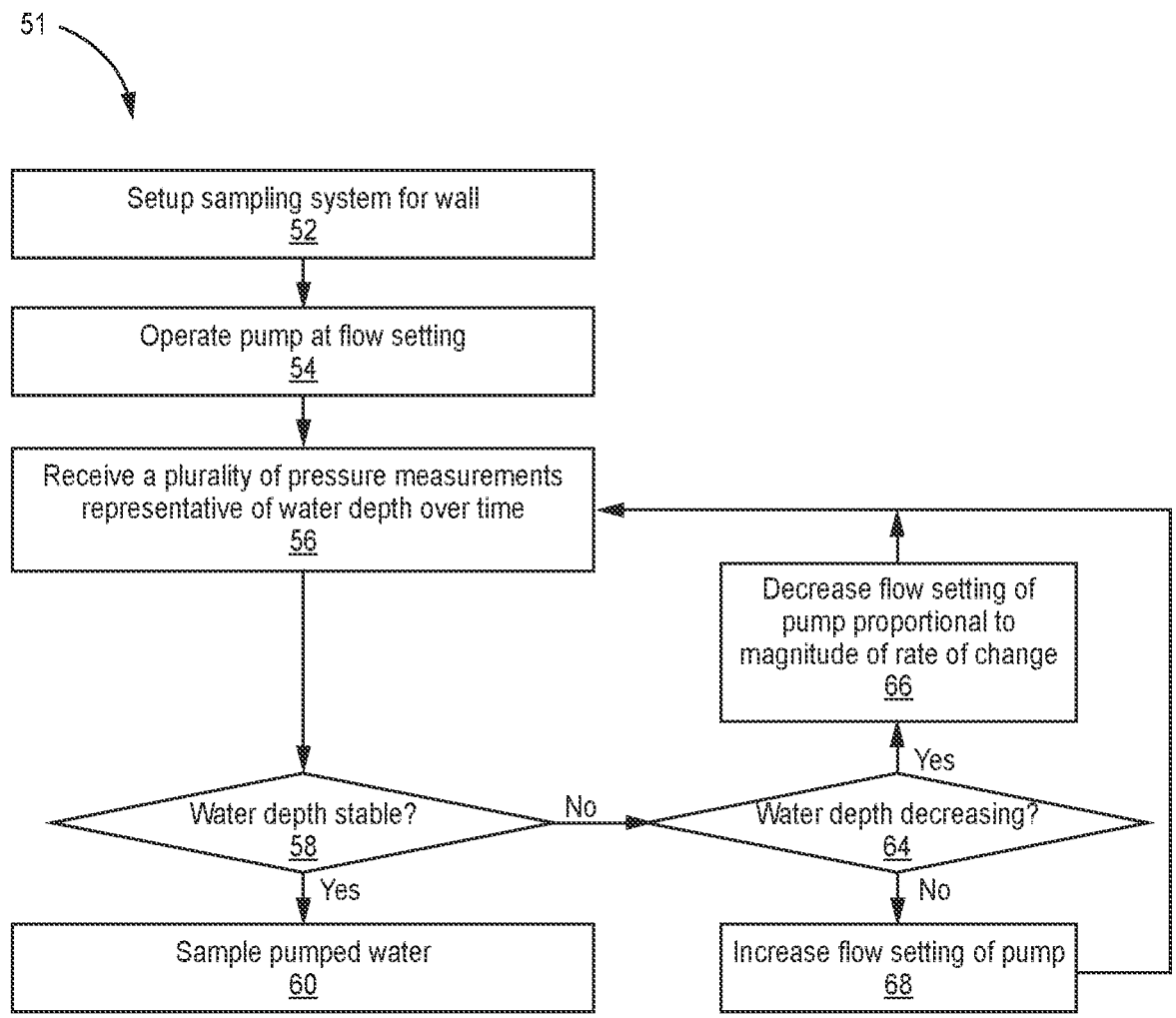
FIG. 4 is another flow chart showing another method of collecting a sample of groundwater from a well.

FIG. 4 is another flow chart showing method 51 of collecting a sample of groundwater from the well. Method 51 is similar to method 50, with steps in method 51 having the same reference numbers as steps in method 50 being the same between the two methods. As such, the discussion will begin with step 64, which is determining if the depth of the groundwater is decreasing 64 after step 58 resulted in a determination that the groundwater depth is unstable. Step 64 could, alternatively, be a determination if the depth of the groundwater is increasing, in which case whether the process advances to step 66 or 68 would be reversed.

If the depth of the groundwater in the well is decreasing (relative to the measurements by the sensor), then method 51 advances to step 66, which is to decrease the flow setting of the pump (and then repeat steps 56 and 58). The controller can perform step 66 such that the flow setting of the pump is decreased proportionally to the degree of the rate of change of the depth of the groundwater as measured in step 56. This can be performed as described with regards to step 62 of method 50 in FIG. 3. For example, a large decrease in the depth of the groundwater can result in a large decrease in the flow setting of the pump, while a small decrease in the depth of the groundwater can result in a small decrease in the flow setting of the pump. After the flow setting of the pump is changed/adjusted 66, method 51 repeats steps 56 and 58.

If the depth of the groundwater in the well is increasing, method 51 advances to step 68, which is increasing the flow setting of the pump. The controller can perform step 68 such that the flow setting of the pump in increased proportionally to the degree of the rate of change of the depth of the groundwater as measured in step 56, or the increase can be a predetermined incremental amount. This can be performed as described with regards to step 62 of method 50 in FIG. 3. For example, a large increase in the depth of the groundwater can result in a large increase in the flow setting of the pump (i.e., the pump removes groundwater from the well at a greater rate), while a small increase in the depth of the groundwater can result in a small increase in the flow setting of the pump. After the flow setting of the pump is changed/adjusted 68, method 51 repeats steps 56 and 58. With both steps 66 and 68, method 51 loops iteratively until the groundwater depth is determined to be stable during step 58. When the depth of the groundwater has stabilized, step 60 is performed and the sample of the groundwater is collected.

In some embodiments of the groundwater sampling method 50/51 and groundwater sampling system 8, the controller can implement a limit of total groundwater depth/level drawdown regardless of whether the depth of the groundwater in the well stabilizes. For example, if the depth of the groundwater decreases a predetermined amount, such as two feet, the controller does not further increase the flow rate of the pump.

Discussion of Possible Embodiments

The following are non-exclusive descriptions of possible embodiments of the present invention.

A system for sampling groundwater from a well that includes a pump configured to be at least partially submerged in the groundwater within the well and pump the groundwater out of the well, a sensor configured to output a signal indicative of the depth of the groundwater in the well, and a controller in communication with the sensor. The controller is configured to receive the signal indicative of the depth of the groundwater from the sensor and compensate for groundwater ingress into the well by adjusting a rate of flow of groundwater pumped by the pump based on the signal to stabilize the depth of groundwater in the well while the pump is pumping groundwater from the well.

The system of the preceding paragraph can optionally include, additionally and/or alternatively, any one or more of the following features, configurations, steps, and/or additional components:

The controller is configured to supply power to the pump to operate the pump and module the level of power to adjust the rate of flow.

The controller is configured to change a level of power supplied to the pump based on the signal by changing the power supplied to the pump in proportion to the rate of change of depth of the groundwater.

The controller is configured to reduce the level of power supplied to the pump by a first amount when the rate of change of depth drawdown of the groundwater is relatively high, and by a second amount when the rate of change of depth drawdown of the groundwater is relatively low, where the first amount is greater than the second amount.

The controller is configured to decrease the level of power supplied to the pump if the signal indicates that the depth of groundwater is decreasing and increase the level of power supplied to the pump if the signal indicates that the depth of groundwater is increasing.

An analyzer in fluid communication with the pump and configured to test the groundwater for indicator parameters indicative of water quality.

The analyzer is in communication with the controller, and the controller is configured to instruct the analyzer to begin testing the groundwater.

The analyzer is configured to collect a sample of the groundwater for analysis after the pump has removed at least a volume of groundwater equal to a volume of a flow zone within the well.

The pump is pneumatically operated and the controller is configured to supply pressurized gas to the pump.

The pump is electrically operated and the controller is configured to supply electricity to the pump.

The controller includes an interface configured to receive commands from a user.

The sensor is one of a pressure transducer and an ultrasonic device in communication with the controller.

A method of collecting a sample of groundwater from a well that includes operating a pump in the well at a flow rate to remove groundwater from the well, repeatedly measuring a depth of the groundwater in the well and communicating signals indicative of the depth of the groundwater to a controller, adjusting the flow rate of the pump by the controller based on the signals indicative of the depth of the groundwater, and collecting the sample of the groundwater when the depth of the groundwater is stable. The controller decreases the flow rate of the pump if the depth of the groundwater is decreasing and increases the flow rate of the pump if the depth of the groundwater is increasing to compensate for ingress of groundwater into the well.

The method of the preceding paragraph can optionally include, additionally and/or alternatively, any one or more of the following features, configurations, steps, and/or additional components:

The step of supplying power to the pump by the controller, wherein the controller changes a level of power supplied to the pump based on the signals indicative of the depth of the groundwater.

The step of reducing the power supplied to the pump by a first amount when the rate of change of depth of the groundwater is relatively high, and by a second amount when the rate of change of depth of the groundwater is relatively low, where the first amount is greater than the second amount.

The step of analyzing the sample of the groundwater to determine a water quality of the groundwater.

The step of instructing, by the controller, an analyzer that is in fluid communication with the pump to collect the sample of the groundwater.

The well includes a flow zone through which groundwater flows into the well and a stagnant zone through which groundwater does not flow into the well.

The step of removing groundwater equal to a volume of the flow zone of the well prior to collecting the sample of the groundwater.

The step of adjusting the flow rate of the pump so that the depth of the groundwater is stable to ensure that groundwater in the stagnant zone does not flow into the pump positioned in the flow zone.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for sampling groundwater from a well, the system comprising:
a pump configured to be at least partially submerged in the groundwater within the well and pump the groundwater out of the well;
a sensor configured to output a signal indicative of the depth of the groundwater in the well; and
a controller in communication with the sensor, the controller configured to receive the signal indicative of the depth of the groundwater from the sensor and compensate for groundwater ingress into the well by adjusting a rate of flow of groundwater pumped by the pump based on the signal to stabilize the depth of groundwater in the well while the pump is pumping groundwater from the well,
wherein the controller is configured to supply power to the pump to operate the pump and modulate the level of power to adjust the flow rate, and
wherein the controller is configured to change a level of power supplied to the pump based on the signal by changing the power supplied to the pump in proportion to the rate of change of depth of the groundwater.

2. The system of claim 1, wherein the controller is configured to reduce the level of power supplied to the pump by a first amount when the rate of change of depth drawdown of the groundwater is relatively high, and by a second amount when the rate of change of depth drawdown of the groundwater is relatively low, where the first amount is greater than the second amount.

3. The system of claim 1, wherein the controller is configured to decrease the level of power supplied to the pump if the signal indicates that the depth of groundwater is decreasing and increase the level of power supplied to the pump if the signal indicates that the depth of groundwater is increasing.

4. The system of claim 1, further comprising:
an analyzer in fluid communication with the pump and configured to test the groundwater for indicator parameters indicative of water quality.

5. The system of claim 4, wherein the analyzer is in communication with the controller, and the controller is configured to instruct the analyzer to begin testing the groundwater.

6. The system of claim 4, wherein the analyzer is configured to collect a sample of the groundwater for analysis after the pump has removed at least a volume of groundwater equal to a volume of a flow zone within the well.

7. The system of claim 1, wherein the pump is pneumatically operated and the controller is configured to supply pressurized gas to the pump.

8. The system of claim 1, wherein the pump is electrically operated and the controller is configured to supply electricity to the pump.

9. The system of claim 1, wherein the controller includes an interface configured to receive commands from a user.

10. The system of claim 1, wherein the sensor is one of a pressure transducer and an ultrasonic device in communication with the controller.

11. A method of collecting a sample of groundwater from a well, the method comprising:
operating a pump in the well at a flow rate to remove groundwater from the well;
repeatedly measuring a depth of the groundwater in the well and communicating signals indicative of the depth of the groundwater to a controller;
adjusting the flow rate of the pump by the controller based on the signals indicative of the depth of the groundwater such that the controller decreases the flow rate of the pump in response to the depth of the groundwater decreasing and increases the flow rate of the pump in response to the depth of the groundwater increasing to compensate for ingress of groundwater into the well; and
collecting the sample of the groundwater when the depth of the groundwater is stable with the sample being collected from a flow zone through which the groundwater flows into the well, wherein the controller is configured to supply power to the pump to operate the pump and a level of power supplied to the pump to adjust the flow rate, and wherein the controller is configured to change a level of power supplied to the pump based on the signal by changing the power supplied to the pump in proportion to the rate of change of depth of the groundwater.

12. The method of claim 11, further comprising:

reducing the power supplied to the pump by a first amount when the rate of change of depth of the groundwater is relatively high, and by a second amount when the rate of change of depth of the groundwater is relatively low, where the first amount is greater than the second amount.

13. The method of claim 11, further comprising:

analyzing the sample of the groundwater to determine a water quality of the groundwater.

14. The method of claim 11, further comprising:

instructing, by the controller, an analyzer that is in fluid communication with the pump to collect the sample of the groundwater.

15. The method of claim 11, wherein the well includes the flow zone through which groundwater flows into the well and a stagnant zone through which groundwater does not flow into the well.

16. The method of claim 15, further comprising:

removing groundwater equal to a volume of the flow zone of the well prior to collecting the sample of the groundwater.

17. The method of claim 15, further comprising:

adjusting the flow rate of the pump so that the depth of the groundwater is stable to ensure that groundwater in the stagnant zone does not flow into the pump positioned in the flow zone.

* * * * *